United States Patent [19]

Swietoslawski et al.

[11] 4,112,242

[45] Sep. 5, 1978

[54] PROCESS FOR PRODUCTION OF 4,4-ISOPROPYLIDENE-BIS-2,6-DIBROMO/-PHENOL

[75] Inventors: Janusz Swietoslawski; Andrzej Silowiecki, both of Jaworzno; Aleksander Ratajczak, Katowice; Barbara Nocoń, Wolbrom; Zofia Baniak, Jaworzno, all of Poland

[73] Assignee: Zaklady Chemiczne "Organika-Azot", Jaworzno, Poland

[21] Appl. No.: 790,568

[22] Filed: Apr. 25, 1977

[30] Foreign Application Priority Data

May 4, 1976 [PL] Poland .................................. 189331

[51] Int. Cl.$^2$ ............................................ C07C 37/00
[52] U.S. Cl. ................................................ 568/726
[58] Field of Search ........................ 260/619 A, 623 H

[56] References Cited

U.S. PATENT DOCUMENTS

| 3,012,035 | 12/1961 | Knowles et al. ............. 260/619 A |
| 3,029,291 | 4/1962 | Dietzler ........................ 260/623 H |
| 3,868,423 | 2/1975 | Montanari et al. ............ 260/623 H |
| 3,929,907 | 12/1975 | Janzon et al. ................ 260/619 R |

OTHER PUBLICATIONS

Sprung, "Industrial and Engineering Chemistry", vol. 13, No. 1 (1941), pp. 35–38, Analytical Edition.
Lange, "Handbook of Chemistry", 10th ed. (1961), pp. 1008–1011.

*Primary Examiner*—Joseph E. Evans

[57] ABSTRACT

Tetrabromo bisphenol A is prepared from bisphenol A by reacting it with less than four moles of bromine in organic solvent, with or without water, and with simultaneous or subsequent treatment with alkali metal chlorate.

2 Claims, No Drawings

PROCESS FOR PRODUCTION OF 4,4-ISOPROPYLIDENE-BIS-2,6-DIBROMO-/PHENOL

This invention relates to the production of 4,4'-isopropylidene-bis-/2,6-dibromo/phenol, used widely under the names tetrabromobisphenol A or TBBA in manufacturing of nonflammable plastics and synthetic resins.

In such processes as at present usually carried out, 4,4'-isopropylidene-bis-/2,6-dibromo/phenol is produced from 4,4'-isopropylidene-bisphenol, known also under the names bisphenol A or dian, by reacting it with bromine. Such processes have been described in U.S. Pat. Nos. 3,029,201, 3,182,088, 3,234,289, 3,363,007, 3,546,302; Federal Republic of Germany Patent Specification No. 1,768,444; Belgian Pat. No. 611,069; French Pat. No. 412,959 and USSR Pat. No. 341,790.

In Patent Specifications of the Federal Republic of Germany No. 1,129,957, 1,151,811, 2,041,220 and 2,162,859 disclosed is a process for production of tetrabromobisphenol A incorporating the use of chlorine, while in Patent Specification of the FRG No. 2,227,439 given is a process involving the reaction with bromine and hydrogen peroxide. Disadvantages of the bromination processes lie in their low economics, as half of the bromine used converts into hydrogen bromide, a by-product. Processes incorporating the use of bromine and chlorine have better economics as hydrogen chloride is the by-product. The main difficulties arising in the above processes lie in maintenance of appropriate stoichometry of the introduced reagents. These problems are solved in the bromine-hydrogen peroxide process, where the necessity of using highy concentrated hydrogen peroxide solutions is the only drawback.

The present invention aims at providing a simple process with complete utilisation of bromine for formation of 4,4'-isopropylidene-bis-/2,6-dibromo/phenol.

The present invention resides in a process where each one mole of 4,4'-isopropylidenebisphenol is reacted with less than four moles of bromine, preferably 2,0–2,1 mole, in an organic solvent or an organic solvent-water solution. The reaction products are simultaneously or subsequently treated with alkali metal chlorates, preferably sodium chlorate, and product separated by known methods. It is advantageous to carry out the process in the presense of a mineral acid, as for instance hydrochloric acid, which increases the reaction rate.

The process according to the present invention is further elucidated by the following example.

EXAMPLE

A 500 c.c. reaction vessel equiped with a stirrer, reflux, thermometer and dropping funnel is filled with 68,4 g/0,3 mole/4,4'-isopropylidene-bis-phenol; 100 g methanol and 20 g of concentrated hydrochloric acid. The stirrer is started and 100 g /0,626 mole/ of bromine added dropwise during 30 min. at 30–35° C. Next 43 g /0,2 mole/ of a 50% sodium chlorate water solution is added dropwise during 45 min. at 35°–40° C. The mixture is stirred for 2 hours at 40°–45° C. then cooled to 15° C. the precipirated product filtered off, washed three times with water and dried. The reaction yields 148 g of 4,4'-isopropylidene-bis-/2,6-dibromo/phenol which is 91% of theoretical yield.

We claim:

1. A process for production of 4,4'-isopropylidene-bis-/2,6-dibromo/phenol wherein each one mole of 4,4'-isopropylidenebisphenol reacts with 2,0–2,1 moles of liquid bromine in an organic solvent or organic solvent-water solution at 30°–45° C., significant in that the degree of bromine-utilisation is increased through subsequent treatment with about 0.67 mole of an alkali metal chlorate.

2. A process according to claim 1 wherein the reaction is carried out in presence of a strong mineral acid.

* * * * *